United States Patent
Parramon et al.

(10) Patent No.: US 9,844,674 B2
(45) Date of Patent: *Dec. 19, 2017

(54) SYSTEM AND METHOD FOR DELIVERING MODULATED SUB-THRESHOLD THERAPY TO A PATIENT

(71) Applicant: Boston Scientific Neuromodulation Corporation, Valencia, CA (US)

(72) Inventors: Jordi Parramon, Valencia, CA (US); Bradley L. Hershey, Valencia, CA (US); Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/199,080

(22) Filed: Jun. 30, 2016

(65) Prior Publication Data

US 2016/0310742 A1    Oct. 27, 2016

Related U.S. Application Data

(63) Continuation of application No. 14/601,686, filed on Jan. 21, 2015, now Pat. No. 9,381,359.
(Continued)

(51) Int. Cl.
*A61N 1/00* (2006.01)
*A61N 1/36* (2006.01)
(Continued)

(52) U.S. Cl.
CPC ....... *A61N 1/36164* (2013.01); *A61N 1/0551* (2013.01); *A61N 1/3615* (2013.01);
(Continued)

(58) Field of Classification Search
CPC ............ A61N 1/36164; A61N 1/37247; A61N 1/0551
See application file for complete search history.

(56) References Cited

U.S. PATENT DOCUMENTS

| 5,938,690 A | 8/1999 | Law et al. |
| 5,941,906 A | 8/1999 | Barreras, Sr. et al. |

(Continued)

FOREIGN PATENT DOCUMENTS

| EP | 2567731 A1 | 3/2013 |
| WO | WO-2006019764 A2 | 2/2006 |

(Continued)

OTHER PUBLICATIONS

"U.S. Appl. No. 14/601,686, Non Final Office Action dated Oct. 1, 2015", 8 pgs.

(Continued)

*Primary Examiner* — Robert N Wieland
(74) *Attorney, Agent, or Firm* — Schwegman Lundberg & Woessner, P.A.

(57) ABSTRACT

A neuromodulation system configured for providing sub-threshold neuromodulation therapy to a patient. The neuromodulation system comprises a neuromodulation lead having at least one electrode configured for being implanted along a spinal cord of a patient, a plurality of electrical terminals configured for being respectively coupled to the at least one electrode, modulation output circuitry configured for delivering sub-threshold modulation energy to active ones of the at least one electrode, and control/processing circuitry configured for selecting a percentage from a plurality of percentages based on a known longitudinal location of the neuromodulation lead relative to the spinal cord, computing an amplitude value as a function of the selected percentage, and controlling the modulation output circuitry (Continued)

to deliver sub-threshold modulation energy to the patient at the computed amplitude value.

20 Claims, 9 Drawing Sheets

Related U.S. Application Data

(60) Provisional application No. 61/936,273, filed on Feb. 5, 2014.

(51) Int. Cl.
*A61N 1/372* (2006.01)
*A61N 1/05* (2006.01)

(52) U.S. Cl.
CPC ..... *A61N 1/36071* (2013.01); *A61N 1/36125* (2013.01); *A61N 1/36132* (2013.01); *A61N 1/37247* (2013.01)

(56) References Cited

U.S. PATENT DOCUMENTS

| | | | |
|---|---|---|---|
| 6,393,325 | B1 | 5/2002 | Mann et al. |
| 6,516,227 | B1 | 2/2003 | Meadows et al. |
| 6,675,046 | B2 | 1/2004 | Holsheimer |
| 6,895,280 | B2 | 5/2005 | Meadows et al. |
| 6,993,384 | B2 | 1/2006 | Bradley et al. |
| 7,317,948 | B1 | 1/2008 | King et al. |
| 7,333,857 | B2 | 2/2008 | Campbell |
| 7,539,538 | B2 | 5/2009 | Parramon et al. |
| 7,627,384 | B2 | 12/2009 | Ayal et al. |
| 7,650,184 | B2 | 1/2010 | Walter |
| 7,979,133 | B2 | 7/2011 | Feler et al. |
| 7,987,000 | B2 | 7/2011 | Moffitt et al. |
| 8,010,198 | B2 | 8/2011 | Libbus et al. |
| 8,019,439 | B2 | 9/2011 | Kuzma et al. |
| 8,160,328 | B2 | 4/2012 | Goetz et al. |
| 8,180,129 | B2 | 5/2012 | Goetz et al. |
| 8,224,453 | B2 | 7/2012 | De Ridder |
| 8,255,057 | B2 | 8/2012 | Fang et al. |
| 8,355,797 | B2 | 1/2013 | Caparso et al. |
| 8,380,318 | B2 | 2/2013 | Kishawi et al. |
| 8,412,345 | B2 | 4/2013 | Moffitt |
| 8,437,857 | B2 | 5/2013 | Moffitt et al. |
| 8,455,716 | B2 | 6/2013 | Huang et al. |
| 8,504,147 | B2 | 8/2013 | Deem et al. |
| 8,594,785 | B2 | 11/2013 | Bradley |
| 8,615,300 | B2 | 12/2013 | Feler et al. |
| 8,644,947 | B2 | 2/2014 | Zhu et al. |
| 8,649,874 | B2 | 2/2014 | Alataris et al. |
| 8,660,653 | B2 | 2/2014 | Kothandaraman |
| 8,670,831 | B2 | 3/2014 | Wacnik et al. |
| 8,676,329 | B2 | 3/2014 | Wacnik et al. |
| 8,676,331 | B2 | 3/2014 | Parker |
| 8,700,178 | B2 | 4/2014 | Anderson |
| 8,706,250 | B2 | 4/2014 | Zhu et al. |
| 8,731,675 | B2 | 5/2014 | Ranu et al. |
| 8,751,009 | B2 | 6/2014 | Wacnik |
| 8,788,054 | B2 | 7/2014 | Kothandaraman et al. |
| 8,909,350 | B2 | 12/2014 | Lee |
| 9,381,359 | B2 | 7/2016 | Parramon et al. |
| 2003/0139781 | A1 | 7/2003 | Bradley et al. |
| 2004/0116978 | A1 | 6/2004 | Bradley |
| 2005/0209655 | A1 | 9/2005 | Bradley et al. |
| 2007/0150036 | A1 | 6/2007 | Anderson |
| 2008/0188909 | A1 | 8/2008 | Bradley |
| 2009/0196472 | A1 | 8/2009 | Goetz et al. |
| 2009/0198306 | A1 | 8/2009 | Goetz et al. |
| 2009/0204173 | A1 | 8/2009 | Fang et al. |
| 2010/0010566 | A1 | 1/2010 | Thacker et al. |
| 2010/0121409 | A1 | 5/2010 | Kothandaraman et al. |
| 2010/0249875 | A1 | 9/2010 | Kishawi et al. |
| 2010/0274312 | A1 | 10/2010 | Alataris et al. |
| 2010/0274314 | A1 | 10/2010 | Alataris et al. |
| 2010/0274315 | A1 | 10/2010 | Alataris et al. |
| 2010/0274317 | A1 | 10/2010 | Parker et al. |
| 2010/0274318 | A1 | 10/2010 | Walker et al. |
| 2010/0274326 | A1 | 10/2010 | Chitre et al. |
| 2010/0305660 | A1* | 12/2010 | Hegi ............... A61N 1/37247 607/60 |
| 2011/0282414 | A1 | 11/2011 | Kothandaraman et al. |
| 2012/0059446 | A1 | 3/2012 | Wallace et al. |
| 2012/0083709 | A1 | 4/2012 | Parker et al. |
| 2012/0253422 | A1 | 10/2012 | Thacker et al. |
| 2012/0265279 | A1 | 10/2012 | Zhu et al. |
| 2012/0283797 | A1 | 11/2012 | De Ridder |
| 2012/0290041 | A1 | 11/2012 | Kim et al. |
| 2013/0066411 | A1 | 3/2013 | Thacker et al. |
| 2013/0116752 | A1 | 5/2013 | Parker et al. |
| 2013/0131760 | A1 | 5/2013 | Rao et al. |
| 2013/0268021 | A1 | 10/2013 | Moffitt |
| 2013/0296975 | A1 | 11/2013 | Lee et al. |
| 2014/0081349 | A1 | 3/2014 | Lee |
| 2014/0277267 | A1 | 9/2014 | Vansickle et al. |
| 2014/0364920 | A1 | 12/2014 | Doan et al. |
| 2015/0217116 | A1 | 8/2015 | Parramon et al. |

FOREIGN PATENT DOCUMENTS

| | | |
|---|---|---|
| WO | WO-2006029257 A2 | 3/2006 |
| WO | WO-2006135791 A2 | 12/2006 |
| WO | WO-2015119773 A1 | 8/2015 |

OTHER PUBLICATIONS

"U.S. Appl. No. 14/601,686, Notice of Allowance dated Mar. 9, 2016", 9 pgs.
"U.S. Appl. No. 14/601,686, Response filed Jan. 4, 2016 to Non Final Office Action dated Oct. 1, 2015", 8 pgs.
"International Application Serial No. PCT/US2015/012190, International Search Report dated Apr. 10, 2015", 5 pgs.
"International Application Serial No. PCT/US2015/012190, Written Opinion dated Apr. 10, 2015", 9 pgs.
He, J, et al., "Perception threshold and electrode position for spinal cord stimulation", Pain, Elsevier Science Publishers, Amsterdam, NL, vol. 59, No. 1, (Oct. 1, 1994), 55-63.
Warman, Eduardo N., et al., "Modeling the Effects of Electric Fields on Nerve Fibers: Determination of Excitation Thresholds", IEEE Transactions on Biomedical Engineering, vol. 39, No. 12, Dec. 1992, (Dec. 1992).
"Australian Application Serial No. 2015214522, First Examiner Report dated Oct. 18, 2016", 3 pgs.
"European Application Serial No. 15702346.6, Response filed to Communication Pursuant to Rules 161(1) and 162 EPC dated Oct. 5, 2016", 7 pgs.
"International Application Serial No. PCT/US2015/012190, International Preliminary Report on Patentability dated Aug. 18, 2016", 10 pgs.

* cited by examiner

| Longitudinal location of neuromodulation lead | Percentage of perception threshold |
|---|---|
| Vertebrae C1- C7 | 30% |
| Vertebrae T1-T12 | 40% |
| Vertebrae L1-L5 | 50% |
| Vertebrae S1-S5 | 60% |

FIG. 9

SYSTEM AND METHOD FOR DELIVERING MODULATED SUB-THRESHOLD THERAPY TO A PATIENT

CLAIM OF PRIORITY

This application is a continuation of U.S. application Ser. No. 14/601,686, filed Jan. 21, 2015, now U.S. Pat. No. 9,381,359, which claims the benefit of priority under 35 U.S.C. §119(e) of U.S. Provisional Patent Application Ser. No. 61/936,273, filed on Feb. 5, 2014, each of which is herein incorporated by reference in its entirety.

FIELD OF THE INVENTION

The present inventions relate to tissue modulation systems, and more particularly, to programmable neuromodulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrode carrying stimulation leads, which are implanted at the desired stimulation site, and an implantable neuromodulation device (e.g., an implantable pulse generator (IPG)) implanted remotely from the stimulation site, but coupled either directly to the neuromodulation lead(s) or indirectly to the neuromodulation lead(s) via a lead extension. The neuromodulation system may further comprise a handheld external control device (e.g., a remote control (RC)) to remotely instruct the neuromodulator to generate electrical stimulation pulses in accordance with selected stimulation parameters.

Electrical modulation energy may be delivered from the neuromodulation device to the electrodes in the form of an electrical pulsed waveform. Thus, electrical energy may be controllably delivered to the electrodes to therapeutically modulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses (which may be considered electrical pulse parameters) provided through the electrode array. Each electrode configuration, along with the electrical pulse parameters, can be referred to as a "modulation parameter set."

With some neuromodulation systems, and in particular, those with independently controlled current or voltage sources, the distribution of the current to the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulation device to generate electrical pulses in accordance with the selected modulation parameters. Typically, the modulation parameters programmed into the neuromodulation device can be adjusted by manipulating controls on the handheld external control device to modify the electrical modulation energy provided by the neuromodulation device system to the patient. Thus, in accordance with the modulation parameters programmed by the external control device, electrical pulses can be delivered from the neuromodulation device to the electrode(s) to modulate a volume of tissue in accordance with a set of modulation parameters and provide the desired efficacious therapy to the patient. The best modulation set will typically be one that delivers modulation energy to the volume of tissue that must be modulated in order to provide the therapeutic benefit (e.g., treatment of pain), while minimizing the volume of non-target tissue that is modulated.

However, the number of electrodes available combined with the ability to generate a variety of complex electrical pulses, presents a huge selection of modulation parameter sets to the clinician or patient. For example, if the neuromodulation system to be programmed has an array of sixteen electrodes, millions of modulation parameter sets may be available for programming into the neuromodulation system. Today, neuromodulation systems may have up to thirty-two electrodes, thereby exponentially increasing the number of modulation parameters sets available for programming.

To facilitate such selection, the clinician generally programs the neuromodulation device through a computerized programming system. This programming system can be a self-contained hardware/software system, or can be defined predominantly by software running on a standard personal computer (PC). The PC or custom hardware may actively control the characteristics of the electrical stimulation generated by the neuromodulation device to allow the optimum stimulation parameters to be determined based on patient feedback or other means and to subsequently program the neuromodulation device with the optimum modulation parameter sets.

For example, in order to achieve an effective result from conventional SCS, the lead or leads must be placed in a location, such that the electrical modulation energy (in this case, electrical stimulation energy) creates a sensation known as paresthesia, which can be characterized as an alternative sensation that replaces the pain signals sensed by the patient. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neuromodulation device to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neuromodulation device (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

Although alternative or artifactual sensations are usually tolerated relative to the sensation of pain, patients sometimes report these sensations to be uncomfortable, and therefore, they can be considered an adverse side-effect to neuromodulation therapy in some cases. Because the perception of paresthesia has been used as an indicator that the applied electrical energy is, in fact, alleviating the pain experienced by the patient, the amplitude of the applied electrical energy is generally adjusted to a level that causes the perception of paresthesia. It has been shown, however, that the delivery of sub-threshold electrical energy (e.g., high frequency pulsed electrical energy and/or low pulse width electrical energy) can be effective in providing neuromodulation therapy for chronic pain without causing paresthesia.

Although sub-threshold modulation therapies have shown good efficacy in early studies, because there is a lack of paresthesia that may otherwise indicate that the delivered sub-threshold electrical energy is optimized, or at least efficacious, it is difficult to immediately determine if the delivered sub-threshold therapy is optimized in terms of providing efficacious therapy. Given that the user cannot rely on the patient's perception of paresthesia, it is often difficult to find the pulse amplitude for the patient that neither under-stimulates the targeted tissue nor accidentally causes the sensation of paresthesia. Thus, finding the optimal set of modulation parameters, especially pulse amplitude, for sub-threshold modulation therapy is often time-consuming and tedious.

There, thus, remains a need to provide a more efficient means to determine the appropriate pulse amplitude for sub-threshold modulation therapy.

SUMMARY OF THE INVENTION

In accordance with a first aspect of the present inventions, a therapeutic neuromodulation system is provided. The neuromodulation system comprises a neuromodulation lead having at least one electrode configured for being implanted along a spinal cord of a patient, a plurality of electrical terminals configured for being respectively coupled to at least one electrode, modulation output circuitry configured for delivered sub-threshold modulation energy (e.g., pulse width less than 100 µs, pulse rate greater than 1500 Hz, etc.) to active ones of the at least one electrode, and control/processing circuitry configured for selecting a percentage from a plurality of percentages based on a known longitudinal location of the neuromodulation lead relative to the spinal cord, computing an amplitude value as a function of the selection percentage, and controlling the modulation output circuitry to deliver sub-threshold modulation energy to the patient at the computed amplitude value.

The selected percentage is a first percentage if the longitudinal location is in a first region of the spinal cord, and the selected percentage is a second percentage if the longitudinal location is in a second region of the spinal cord, wherein the second percentage is higher than the first percentage, and the second region of the spinal cord is caudal to the first region of the spinal cord.

The selected percentage may be a first percentage (20%-60%) if the longitudinal location is in a cervical region of the spinal cord, a second percentage (30%-70%) if the longitudinal location is in a thoracic region of the spinal cord, a third percentage (40%-80%) if the longitudinal location is in a lumbar region of the spinal cord, and a fourth percentage (50%-90%) if the longitudinal location is in a sacral region of the spinal cord. The second percentage is greater than the first percentage, the third percentage is greater than the second percentage, and the fourth percentage is greater than the third percentage.

The control/processing circuitry is configured for computing the amplitude value as a function of the selected percentage and a perception threshold of the patient.

The neuromodulation system further comprises memory configured for storing a look-up table containing a plurality of different percentages and associated neuromodulation lead locations. The percentage is selected by matching the known longitudinal location of the neuromodulation lead relative to the spinal cord with one of the neuromodulation lead locations stored in the look-up table.

The control/processing circuitry may be configured for determining the known longitudinal location of the implanted neuromodulation lead relative to the spinal cord. In an alternate embodiment, the neuromodulation system further comprises a user interface configured for receiving user input defining the known longitudinal location of the implanted neuromodulation lead relative to the spinal cord.

In accordance with a second aspect of the present inventions, an external controller for user with a neuromodulation device coupled to at least one electrode comprising a user interface configured for receiving user input, control/processing circuitry configured for selecting a percentage from a plurality of percentages based on a known longitudinal location of the neuromodulation lead relative to the spinal cord, computing an amplitude value as a function of the selected percentage and output circuitry configured for transmitting the amplitude value to the neuromodulation device.

The amplitude value is computed in the same manner described above. The percentages are selected in the same manner described above. The longitudinal location of the neuromodulation lead is determined in the same manner described above.

In accordance to a third aspect of the present inventions, a method of providing sub-threshold modulation therapy to a patient comprises selecting a percentage from a plurality of percentages based on a known longitudinal location of the neuromodulation lead relative to the spinal cord, computing an amplitude value as a function of the selected percentage, and delivering sub-threshold modulation energy to the patient at the computed amplitude value.

The method of computing the amplitude value is computed is the same as described above. The method of selecting percentages based on the longitudinal location is the same as described above. The longitudinal location of the neuromodulation lead is determined in the same manner described above.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 9 is a table illustrating a plurality of percentages of the perception threshold based on a longitudinal location of the implanted neuromodulation lead of FIG. 3 with respect to the spinal cord.

DETAILED DESCRIPTION OF THE EMBODIMENTS

The description that follows relates to a spinal cord modulation (SCM) system. However, it is to be understood that the while the invention lends itself well to applications in SCM, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
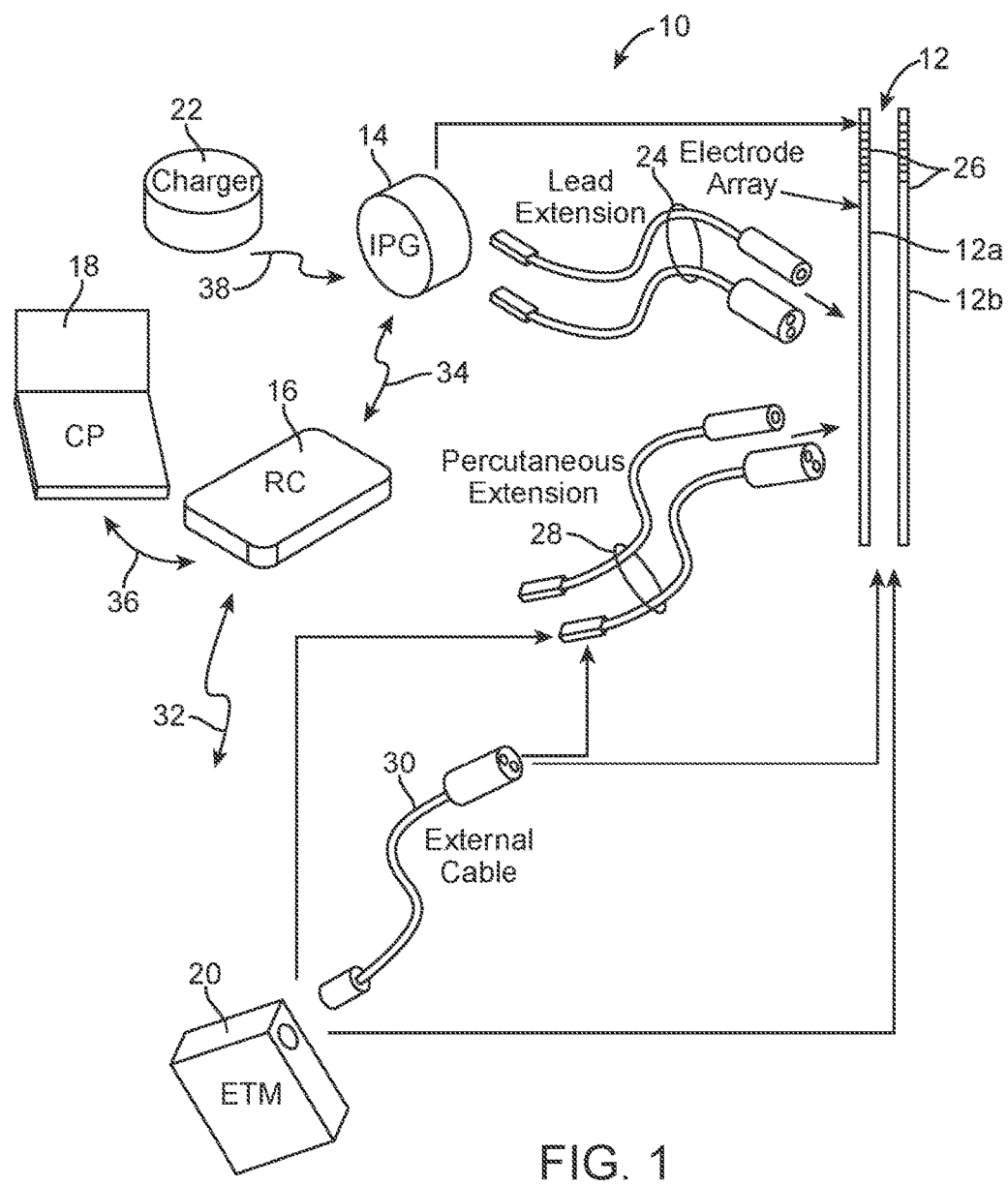
FIG. 1 is a plan view of a Spinal Cord Modulation (SCM) system constructed in accordance with one embodiment of the present inventions.

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20. For purposes of brevity, the details of the ETM 20 will not be described herein.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein.

For purposes of brevity, the details of the RC 16, ETM 20, and external charger 22 will not be described herein. Details of exemplary embodiments of these devices are disclosed in U.S. Pat. No. 6,895,280, which is expressly incorporated herein by reference.

Figure 2:
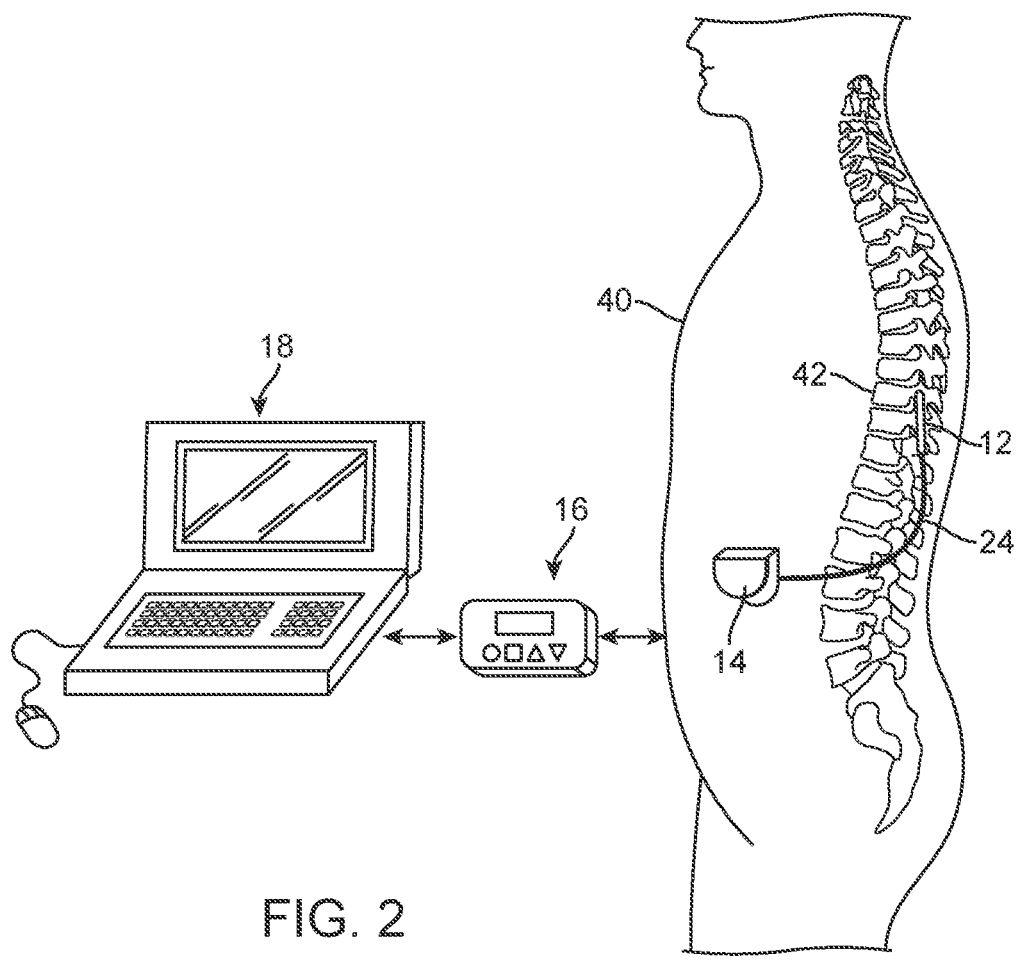
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As there shown, the CP 18 communicates with the IPG 14 via the RC 16.

The IPG 14 comprises an outer case 40 for housing the electronic and other components (described in further detail below), and a connector 42 to which the proximal ends of the neuromodulation leads 12 mate in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a pulse generation circuitry that provides electrical modulation energy to the electrodes 26 in accordance with a set of modulation parameters. Such parameters may include electrode combinations, which define the electrodes that are activated as anodes (positive), cathodes (negative), and turned off (zero). The modulation parameters may further include pulse amplitude (measured in milliamps or volts depending on whether the IPG 14 supplies constant current or constant voltage to the electrodes), pulse width (measured in microseconds), pulse rate (measured in pulses per second), duty cycle (pulse width divided by cycle duration), burst rate (measured as the modulation energy on duration X and modulation energy off duration Y), and pulse shape.

With respect to the pulse patterns provided during operation of the system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG outer case 40. Electrical energy may be transmitted to the tissue in a monopolar or multipolar (for example, bipolar, tripolar and similar configurations) fashion or by any other means available.

The IPG 14 may be operated in either a super-threshold delivery mode or a sub-threshold delivery mode. While in the super-threshold delivery mode, the IPG 14 is configured for delivering electrical modulation energy that provides super-threshold therapy to the patient (in this case, causes the patient to perceive paresthesia). For example, an exemplary super-threshold pulse train may be delivered at a relatively high pulse amplitude (e.g., 5 ma), a relatively low pulse rate (e.g., less than 1500 Hz, preferably less than 500 Hz), and a relatively high pulse width (e.g., greater than 100 μs, preferably greater than 200 μs).

While in the sub-threshold delivery mode, the IPG 14 is configured for delivering electrical modulation energy that provides sub-threshold therapy to the patient (in this case, does not cause the patient to perceive paresthesia). For example, an exemplary sub-threshold pulse train may be delivered at a relatively low pulse amplitude (e.g., 2.5 ma), a relatively high pulse rate (e.g., greater than 1500 Hz, preferably greater than 2500 Hz), and a relatively low pulse width (e.g., less than 100 μs, preferably less than 50 μs).

Figure 3:
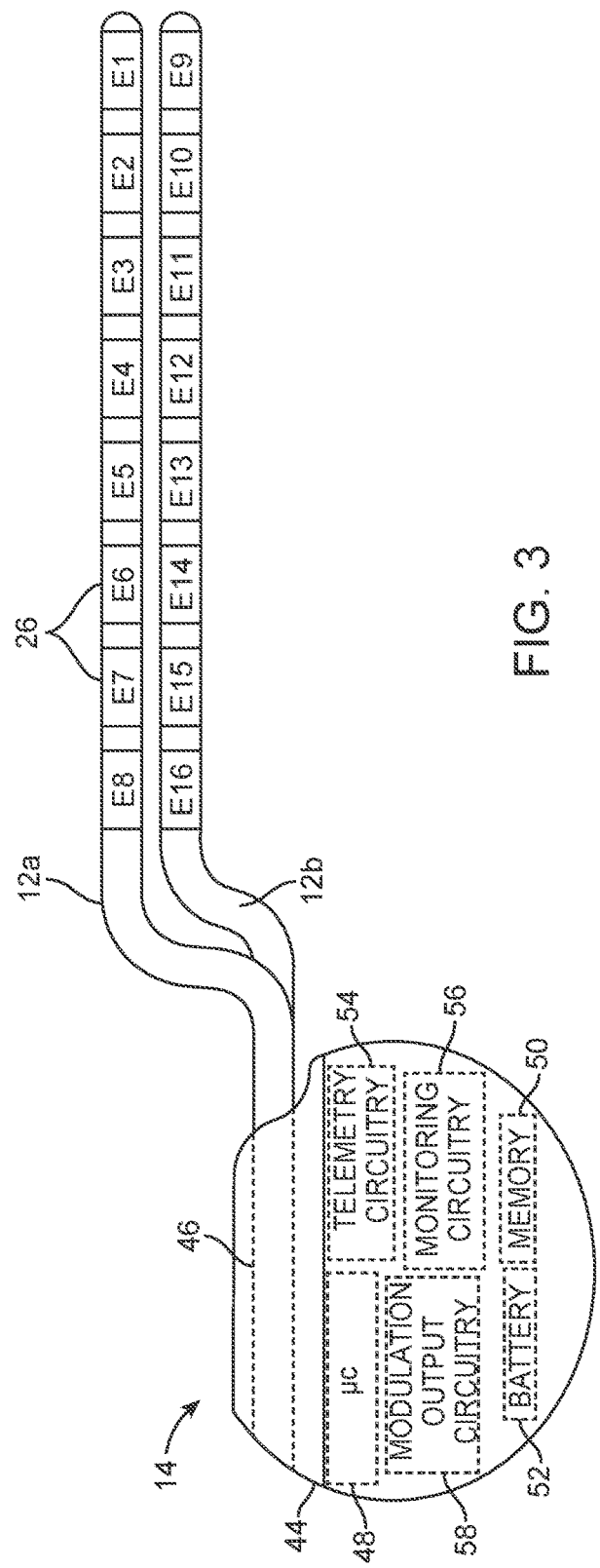
FIG. 3 is a profile view of an implantable pulse generator (IPG) and percutaneous leads used in the SCM system of FIG. 1.

Referring now to FIG. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 comprises electronic components, such as a controller/processor (e.g., a microcontroller) 48, memory 50, a battery 52, telemetry circuitry 54, monitoring circuitry 56, modulation output circuitry 58, and other suitable components known to those skilled in the art. The microcontroller 48 executes a suitable program stored in memory 50, for directing and controlling the neuromodulation performed by IPG 14. Telemetry circuitry 54, including an antenna (not shown), is configured for receiving programming data (e.g., the operating program and/or modulation parameters) from the RC 16 and/or CP 18 in an appropriate modulated carrier signal, which the programming data is then stored in the memory (not shown). The telemetry circuitry 54 is also configured for transmitting status data to the RC 16 and/or CP 18 in an appropriate modulated carrier signal. The battery 52, which may be a rechargeable lithium-ion or lithium-ion polymer battery, provides operating power to IPG 14. The monitoring circuitry 56 is configured for monitoring the present capacity level of the battery 43.

The modulation output circuitry 58 provides electrical modulation energy in the form of a pulsed electrical waveform to the electrodes 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the modulation on duration X and modulation off duration Y).

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12a may be activated as an anode at the same time that electrode E11 on the second lead 12b is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12a may be activated as anodes at the same time that electrode E12 on the second lead 12b is activated as a cathode.

Any of the electrodes E1-E16 and case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (sourcing current), negative (sinking current), or off (no current) polarity in any of the k timing channels.

Figure 4:
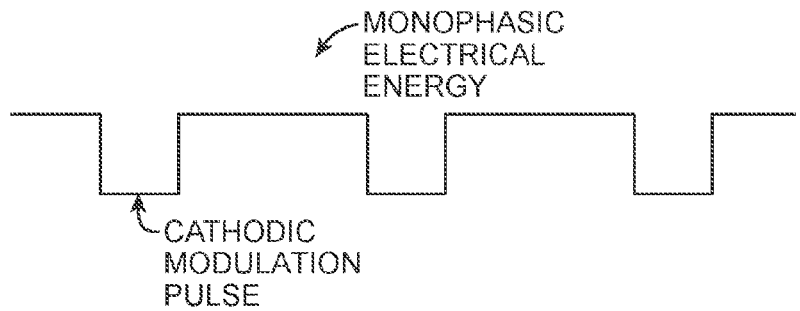
FIG. 4 is a plot of monophasic cathodic electrical modulation energy.

The modulation energy may be delivered between a specified group of electrodes as monophasic electrical energy or multiphasic electrical energy. As illustrated in FIG. 4, monophasic electrical energy takes the form of an electrical pulse train that includes either all negative pulses (cathodic), or alternatively all positive pulses (anodic).

Figure 5A:
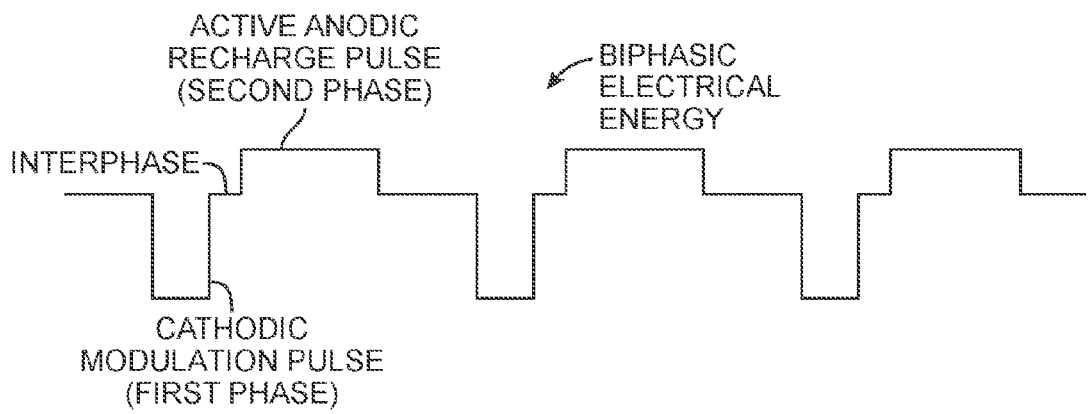
FIG. 5a is a plot of biphasic electrical modulation energy having a cathodic modulation pulse and an active charge recovery pulse.
Figure 5B:
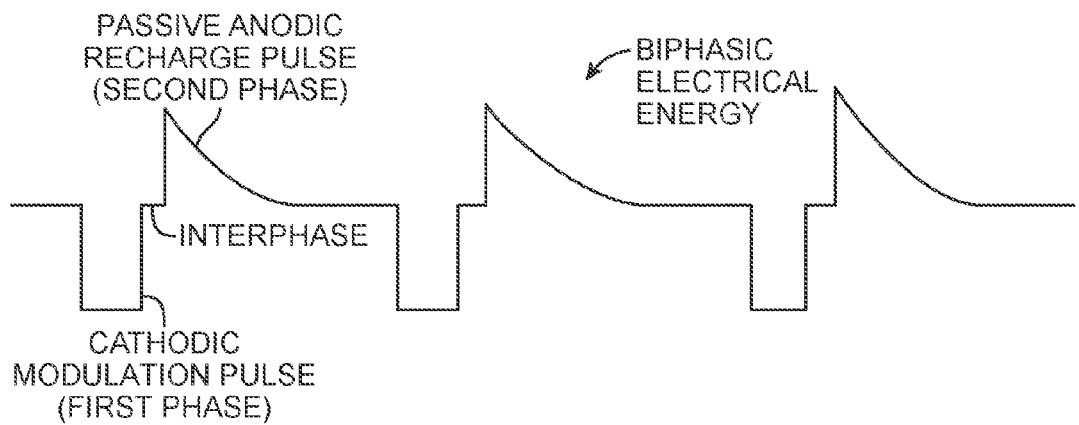
FIG. 5b is a plot of biphasic electrical modulation energy having a cathodic modulation pulse and a passive charge recovery pulse.

Multiphasic electrical energy includes a series of pulses that alternate between positive and negative. For example, as illustrated in FIGS. 5a and 5b, multiphasic electrical energy may include a series of biphasic pulses, with each biphasic pulse including a cathodic (negative) modulation phase and an anodic (positive) charge recovery pulse phase that is generated after the modulation phase to prevent direct current charge transfer through the tissue, thereby avoiding electrode degradation and cell trauma. That is, charge is conveyed through the electrode-tissue interface via current at an electrode during a modulation period (the length of the modulation phase), and then pulled back off the electrode-tissue interface via an oppositely polarized current at the same electrode during a recharge period (the length of the charge recovery phase).

The second phase may be an active charge recovery phase (FIG. 5a), wherein electrical current is actively conveyed through the electrode via current or voltage sources, or the second phase may be a passive charge recovery phase (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds). Although the modulation and charge recovery phases of the biphasic pulses illustrated in FIGS. 5a and 5b are cathodic and anodic, respectively, it should be appreciated that the modulation and charge recovery pulses of biphasic pulses may be anodic and cathodic, respectively, depending upon the desired therapeutic result.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other neuromodulators that may be used with the invention include neuromodulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCM system 10 may alternatively utilize an implantable receiver-stimulator (not shown) connected to the neuromodulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-modulator. The implanted receiver-modulator receives the signal and generates the modulation in accordance with the control signals.

More significant to the present inventions, since the user cannot rely on the patient's perception of paresthesia to select the proper pulse amplitude, the SCM system 10 is configured for automatically determining an appropriate pulse amplitude for a desired sub-threshold modulation program based on a stored algorithm that accounts for a longitudinal location of the implanted neuromodulation lead 12. Thus, instead of manually testing out various pulse amplitudes in an effort to find an optimal pulse amplitude for sub-threshold therapy, the user may rely on the automatically generated pulse amplitude, thereby making the programming process more efficient and time-effective.

Typically, the pulse amplitude for sub-threshold modulation therapy is calculated as a function (e.g., percentage) of the perception threshold (i.e., the amplitude at which the patient perceives paresthesia). Since the goal of sub-threshold modulation therapy is to provide therapy without inducing paresthesia, the sub-threshold amplitude is purposely kept lower than the perception threshold; however, it cannot be so low that the patient receives no therapy at all from the lowered amplitude. For example, the sub-threshold amplitude may be calculated to be 70% of the perception threshold. Or, in another example, the sub-threshold amplitude may be 50% of the perception threshold.

It should be appreciated that the same percentage of the perception threshold may not be equally effective in all situations. For example, sub-threshold therapy having a pulse amplitude of 50% of the perception threshold may be effective in one situation, but may not be effective in another. While the exact mechanisms are not understood, it has been generally observed that a lower percentage of the perception threshold is effective for sub-threshold modulation therapy when the implanted neuromodulation lead 12 is located at an upper region of the spinal cord as compared to when the implanted neuromodulation lead 12 is implanted at a lower region of the spinal cord. In other words, moving down the spinal cord in the caudal direction, a sub-threshold amplitude calculated based on a higher percentage of the perception threshold is typically required for effective sub-threshold therapy.

One theory for this pattern may relate to the amount of gray matter found in the spinal cord at different sections of the spinal cord. As a general rule, the presence of more gray matter means that there are more nerve endings in that particular region, thus making it more likely that neural tissue will get directly stimulated. For example, a smaller percentage of the perception threshold is appropriate when the neuromodulation lead 12 is implanted in the thoracic region as compared to when the neuromodulation lead 12 is implanted in the sacral region. Based on this observed pattern, the SCM system 10 is configured for automatically selecting an appropriate percentage of the perception threshold based on the longitudinal location of the implanted neuromodulation lead 12. It should be appreciated that the user may either rely on the automatically generated percentage, or instead treat it as a suggestion, based on which to program the IPG 14 with the appropriate modulation parameters for sub-threshold modulation therapy.

Figure 6:
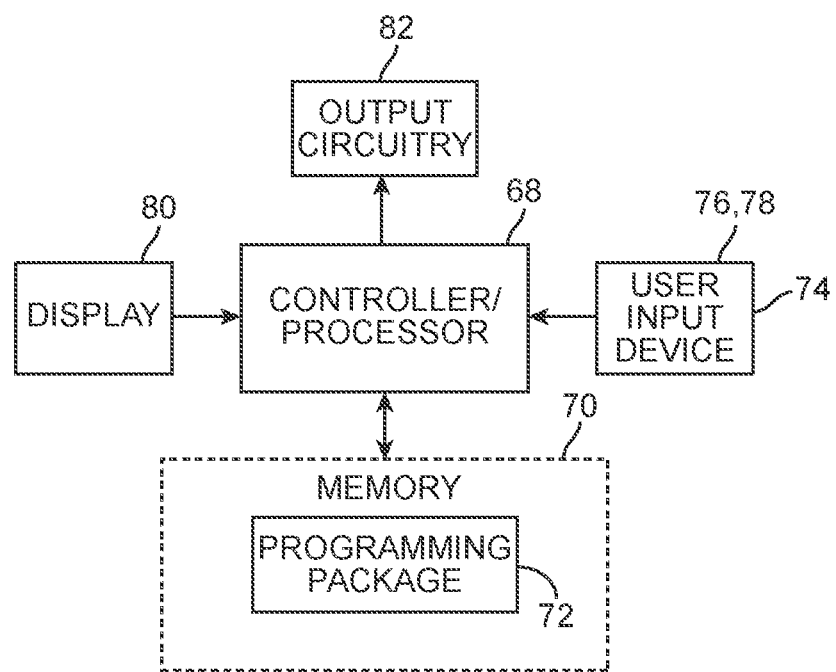
FIG. 6 is a block diagram of a clinician's programmer (CP) used in the SCM system of FIG. 1.

In practice, the user performs these programming sessions of the IPG 14 on the CP 18. As shown in FIG. 6, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical modulation generated by the IPG 14 to allow the optimum modulation parameters to be determined based on patient feedback and for subsequently programming the IPG 14 with the optimum modulation parameter.

To allow the user to perform these functions, the CP 18 includes a user input device (e.g., a mouse 76 and a keyboard 78), and a programming display screen 80 housed in a case 82. It is to be understood that in addition to, or in lieu of, the mouse 76, other directional programming devices may be used, such as a trackball, touchpad, joystick, or directional keys included as part of the keys associated with the keyboard 78.

In the illustrated embodiment described below, the display screen 80 takes the form of a conventional screen, in which case, a virtual pointing device, such as a cursor controlled by a mouse, joy stick, trackball, etc., can be used to manipulate graphical objects on the display screen 80. In alternative embodiments, the display screen 80 takes the form of a digitizer touch screen, which may either passive or active. Further details discussing the use of a digitizer screen for programming are set forth in U.S. Provisional Patent Application Ser. No. 61/561,760, entitled "Technique for Linking Electrodes Together during Programming of Neurostimulation System," which is expressly incorporated herein by reference.

Referring now to FIG. 6, the CP 18 includes a controller/processor 68 (e.g., a central processor unit (CPU)) and memory 70 that stores a programming package 72, which can be executed by the controller/processor 68 to allow the user to program the IPG 14 and RC 16. The CP 18 further includes a user input device 74 (such as the mouse 76 or the keyboard 78 described above) to provide user commands. Notably, while the controller/processor 68 is shown in FIG. 6 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by the microcontroller 48 of the IPG 14 or the processor of the RC 16.

Execution of the programming package 72 by the controller/processor 68 provides a multitude of display screens (not shown) that can be navigated through via use of the mouse 76. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), define the configuration and orientation of the leads, initiate and control the electrical modulation energy output by the neuromodulation leads 12, and select and program the IPG 14 with modulation parameters in both a surgical setting and a clinical setting. Further details discussing the above-described CP functions are disclosed in U.S. patent application Ser. No. 12/501,282, now issued as U.S. Pat. No. 9,278,222, entitled "System and Method for Converting Tissue Stimulation Programs in a Format Usable by an Electrical Current Steering Navigator," and U.S. patent application Ser. No. 12/614,942, now U.S. Patent Publication No. 2010/0121409, entitled "System and Method for Determining Appropriate Steering Tables for Distributing Modulation energy Among Multiple Neuromodulation Electrodes," which are expressly incorporated herein by reference. Execution of the programming package 72 provides a user interface that conveniently allows a user to program the IPG 14.

Figure 7:
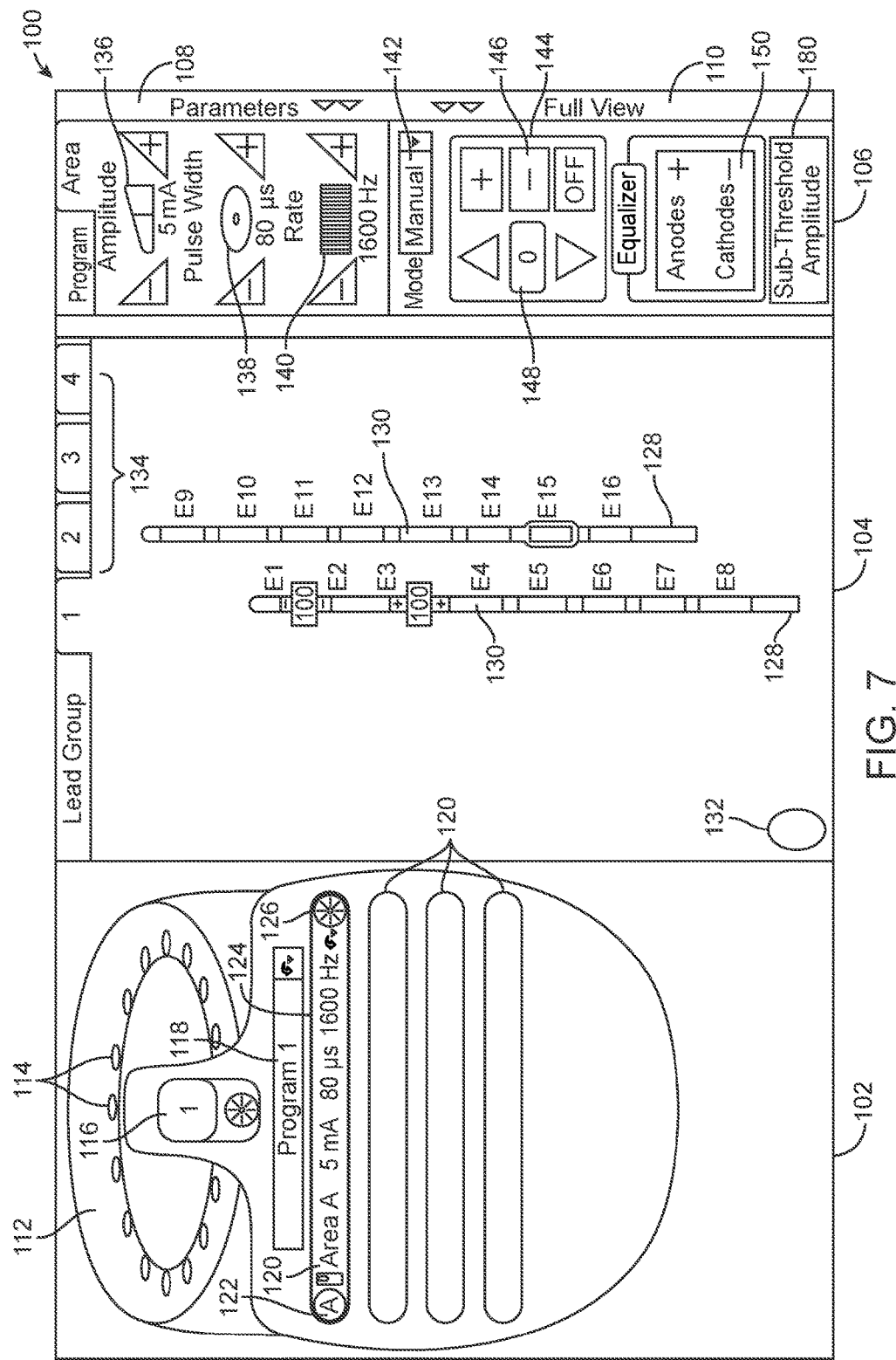
FIG. 7 is a plan view of a user interface of the CP of FIG. 6 for programming the IPG of FIG. 3 in a manual programming mode.

Referring now to FIG. 7, a programming screen 100 that can be generated by the CP 18 to allow a user to program the IPG 14 will be described. In the illustrated embodiment, the programming screen 100 comprises three panels: a program selection panel 102, a lead display panel 104, and a modulation parameter adjustment panel 106. Some embodiments of the programming screen 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about modulation programs and coverage areas that have been, or may be, defined for the IPG 14. In particular, the program selection panel 102 includes a carousel 112 on which a plurality of modulation programs 114 (in this case, up to sixteen) may be displayed and selected. The program selection panel 102 further includes a selected program status field 116 indicating the number of the modulation program 114 that is currently selected (any number from "1" to "16"). In the illustrated embodiment, program 1 is the only one currently selected, as indicated by the number "1" in the field 116. The program selection panel 102 further comprises a name field 118 in which a user may associate a unique name to the currently selected modulation program 114.

The program selection panel 102 further comprises a plurality of coverage areas 120 (in this case, up to four) with which a plurality of modulation parameter sets can respectively be associated to create the currently selected modulation program 114 (in this case, program 1). Each coverage area 120 that has been defined includes a designation field 122 (one of letters "A"-"D"), and an electrical pulse parameter field 124 displaying the electrical pulse parameters, and specifically, the pulse amplitude, pulse width, and pulse rate, of the modulation parameter set associated with the that coverage area. In this example, only coverage area A is defined for program 1, as indicated by the "A" in the designation field 122. The electrical pulse parameter field 124 indicates that a pulse amplitude of 5 mA, a pulse width of 80 µs, and a pulse rate of 1600 Hz has been associated with coverage area A.

Each of the defined coverage areas 120 also includes a selection icon 126 that can be alternately actuated to activate or deactivate the respective coverage area 120. When a coverage area is activated, an electrical pulse train is delivered from the IPG 14 to the electrode array 26 in accordance with the modulation parameter set associated with that coverage area. Notably, multiple ones of the coverage areas 120 can be simultaneously activated by actuating the selection icons 126 for the respective coverage areas. In this case, multiple electrical pulse trains are concurrently delivered from the IPG 14 to the electrode array 26 during timing channels in an interleaved fashion in accordance with the respective modulation parameter sets associated with the coverage areas 120. Thus, each coverage area 120 corresponds to a timing channel.

To the extent that any of the coverage areas 120 have not been defined (in this case, three have not been defined), they include text "click to add another program area"), indicating that any of these remaining coverage areas 120 can be selected for association with a modulation parameter set. Once selected, the coverage area 120 will be populated with the designation field 122, electrical pulse parameter field 124, and selection icon 126.

The parameter adjustment panel 106 includes a pulse amplitude adjustment control 136 (expressed in milliamperes (mA)), a pulse width adjustment control 138 (expressed in microseconds (µs)), and a pulse rate adjustment control 140 (expressed in Hertz (Hz)), which are displayed and actuatable in all the programming modes. Each of the controls 136-140 includes a first arrow that can be actuated to decrease the value of the respective modulation parameter and a second arrow that can be actuated to increase the value of the respective modulation parameter. Each of the controls 136-140 also includes a display area for displaying the currently selected parameter. In response to the adjustment of any of electrical pulse parameters via manipulation of the graphical controls in the parameter adjustment panel 106, the controller/processor 68 generates a corresponding modulation parameter set (with a new pulse amplitude, new pulse width, or new pulse rate) and transmits it to the IPG 14 via the telemetry circuitry 54 for use in delivering the modulation energy to the electrodes 26.

The parameter adjustment panel 106 includes a pull-down programming mode field 142 that allows the user to switch between a manual programming mode, an electronic trolling programming mode, and a navigation programming mode. Each of these programming modes allows a user to define a modulation parameter set for the currently selected coverage area 120 of the currently selected program 114 via manipulation of graphical controls in the parameter adjustment panel 106 described above, as well as the various graphical controls described below.

The manual programming mode is designed to allow the user to manually define the fractionalized electrical current for the electrode array with maximum flexibility; the electronic trolling programming mode is designed to quickly sweep the electrode array using a limited number of electrode configurations to gradually steer an electrical field relative to the neuromodulation leads until the targeted modulation site is located; and the navigation programming mode is designed to sweep the electrode array using a wide number of electrode configurations to shape the electrical field, thereby fine tuning and optimization the modulation coverage for patient comfort.

As shown in FIG. 7, the manual programming mode has been selected. In the manual programming mode, each of the electrodes 130 of the graphical leads 128, as well as the graphical case 132, may be individually selected, allowing the clinician to set the polarity (cathode or anode) and the magnitude of the current (percentage) allocated to that electrode 130, 132 using graphical controls located in an amplitude/polarity area 144 of the parameter adjustment panel 106.

In particular, a graphical polarity control 146 located in the amplitude/polarity area 144 includes a "+" icon, a "−" icon, and an "OFF" icon, which can be respectively actuated to toggle the selected electrode 130, 132 between a positive polarization (anode), a negative polarization (cathode), and an off-state. An amplitude control 148 in the amplitude/polarity area 144 includes an arrow that can be actuated to decrease the magnitude of the fractionalized current of the selected electrode 130, 132, and an arrow that can be actuated to increase the magnitude of the fractionalized current of the selected electrode 130, 132. The amplitude control 148 also includes a display area that indicates the adjusted magnitude of the fractionalized current for the selected electrode 134. The amplitude control 148 is preferably disabled if no electrode is visible and selected in the lead display panel 104. In response to the adjustment of fractionalized electrode combination via manipulation of the graphical controls in the amplitude/polarity area 144, the controller/processor 68 generates a corresponding modulation parameter set (with a new fractionalized electrode combination) and transmits it to the IPG 14 via the telemetry circuitry 54 for use in delivering the modulation energy to the electrodes 26.

In the illustrated embodiment, electrode E1 has been selected as a cathode and electrode E3 has been selected as anode with 100% of the cathodic and anodic current allocated to each of them respectively. Although the graphical controls located in the amplitude/polarity area 144 can be manipulated for any of the electrodes, a dedicated graphical control for selecting the polarity and fractionalized current value can be associated with each of the electrodes, as described in U.S. Patent Publication No. 2012/0290041, entitled "Neurostimulation System with On-Effector Programmer Control," which is expressly incorporated herein by reference.

The parameter adjustment panel 106, when the manual programming mode is selected, also includes an equalization control 150 that can be actuated to automatically equalize current allocation to all electrodes of a polarity selected by respective "Anode +" and "Cathode −" icons.

Significant to the present inventions, the parameter adjustment panel 106 also comprises a sub-threshold amplitude control 180 that can be actuated to automatically generate an appropriate sub-threshold amplitude based on the longitudinal location of the implanted neuromodulation lead 12. In the illustrated embodiment, actuating the sub-threshold amplitude control 180 will determine the sub-threshold amplitude for the selected sub-threshold program, "Program 1" as shown in the program selection control 102, having a pulse width of 80 µs and pulse rate of 1600 Hz as shown in the parameter adjustment panel 106. It should be appreciated that the user may originally select a pulse amplitude (5 mA as illustrated), which is then automatically modified after the sub-threshold amplitude control 180 is actuated. The sub-threshold modulation program is typically selected based on the patient's individual needs and targeted area for neuromodulation therapy. Although the following discussion will focus on the selected sub-threshold modulation program (Program 1), it should be appreciated that the user may manually select modulation parameters in the parameter adjustment panel 106 without relying on existing programs in the program selection panel 102.

Figure 8:
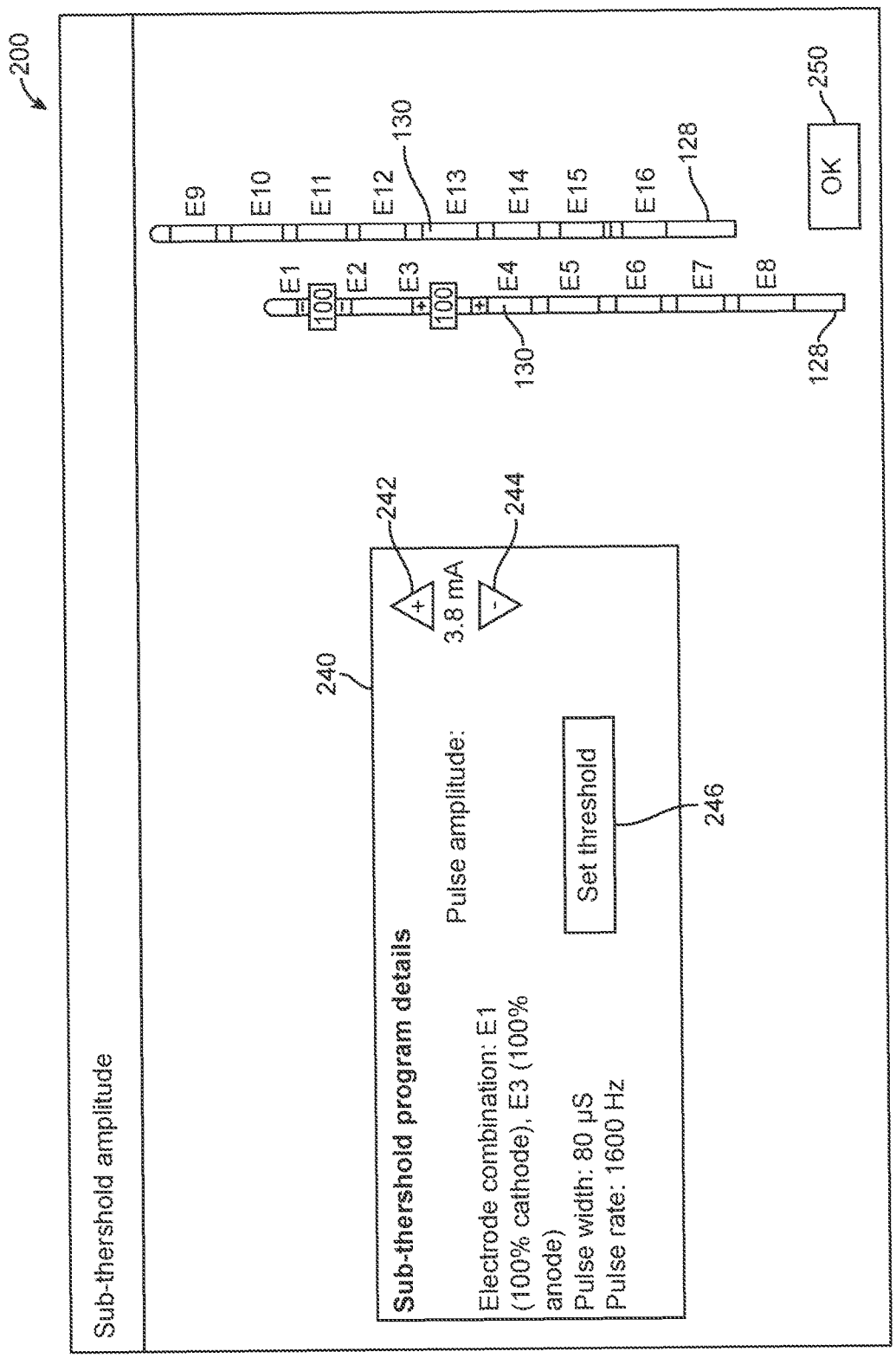
FIG. 8 is a plan view of a user interface of the CP of FIG. 6 illustrating a perception threshold program screen for determining a perception threshold.

When the sub-threshold modulation amplitude control 180 is actuated, the user is automatically taken to a sub-threshold modulation amplitude determination screen 200 as shown in FIG. 8. The main function of the sub-threshold amplitude determination screen 200 is to determine the perception threshold of the selected sub-threshold modulation program (Program 1, in this case), and to calculate the sub-threshold amplitude based on the perception threshold and the longitudinal location of the implanted neuromodulation lead 12.

It should be appreciated that the longitudinal location of the implanted neuromodulation lead 12 is typically determined at the very start of the programming process (not illustrated), and once it is determined, it is stored in the memory 70. In the preferred embodiment, the SCM system 10 is configured for automatically determining the longitudinal location of the implanted neuromodulation lead 12. More specifically, the SCM system 10 may be configured to apply image recognition techniques to a stored medical image (e.g., MRI scan, CT scan, fluoroscopy, etc.) of the patient's spinal cord, and identify the longitudinal location of the implanted neuromodulation lead 12 with respect to the spinal cord.

In an alternate embodiment, the SCM system 10 may be configured to aid the user in determining the longitudinal location of the implanted neuromodulation lead. More specifically, the user may view the stored medical image of the patient's spinal cord and manually input the longitudinal location of the neuromodulation lead 12. In either case, the longitudinal location of the neuromodulation lead 12 is stored in the memory, based on which the following sub-threshold amplitude is calculated after the perception threshold is determined in the sub-threshold amplitude determination screen 200.

As shown in FIG. 8, the sub-threshold amplitude screen 200 includes graphical leads 128 having graphical electrodes 130 that illustrate the electrode combination of the selection program. As per the selected sub-threshold modulation program, Program 1, graphical electrodes E1 and E3 are shown as being selected. The sub-threshold amplitude screen 200 also includes a perception threshold determination panel 240. As shown in the illustrated embodiment, the perception threshold determination panel 240 also displays the details of the selected sub-threshold modulation program, including electrode combination, pulse width, pulse rate, polarity, etc. More importantly, the perception threshold determination panel allows the user to determine the perception threshold for the selected sub-threshold modulation program.

To determine the perception threshold, the pulse amplitude is incrementally increased using graphical control 242 until the patient reports a feeling of paresthesia, at which point, the "Set Threshold" control 246 can be actuated such that that particular amplitude value at which paresthesia was first perceived is automatically recorded. In the illustrated embodiment, the amplitude has been incrementally increased to reach a pulse amplitude of 3.8 mA, which is set as the perception threshold.

Based on the determined perception threshold, the CP 18 is configured to automatically calculate the sub-threshold amplitude for that sub-threshold modulation program based on the perception threshold and the determined longitudinal location of the implanted neuromodulation lead 12.

To this end, the SCM system 10 may refer to a stored look-up table containing a list of different longitudinal locations of the neuromodulation lead 12, each of which corresponds to an appropriate percentage of the perception threshold that can be used to calculate the sub-threshold amplitude. The look-up table typically contains a list of vertebral levels, each of which encompasses several vertebrae that correspond to the same percentage.

For example, there may be four vertebral levels: cervical level (C1-C7), thoracic level (T1-T12), lumbar level (L1-L5) and sacral level (S1-S5). Or, in another example, the look-up table may be even more granular, and comprise more vertebral levels to account for more subtle differences: cervical level 1 (C1-C3), cervical level 2 (C4-C7), thoracic level 1 (T1-T6), etc. In yet another example, to be even more precise, every vertebra of the vertebral column might constitute its own vertebral level (C1 level, C2 level, C3 level, etc.).

Referring now to FIG. 9, one exemplary embodiment of how the CP 18 selects the percentage of the perception threshold based on the longitudinal location of the implanted neuromodulation lead 12 is illustrated. If the determined longitudinal location of the implanted neuromodulation lead 12 is the cervical region of the vertebral column (C1-C7), the selected percentage of the perception threshold from which to calculate the sub-threshold amplitude is 30%. If the determined longitudinal location of the implanted neuromodulation lead 12 is the thoracic region of the vertebral column (T1-T12), the selected percentage of the perception threshold from which to calculate the sub-threshold amplitude is 40%. If the determined longitudinal location of the implanted neuromodulation lead 12 is the lumbar region of the vertebral column (L1-L5), the selected percentage of the perception threshold from which to calculate the sub-threshold amplitude is 50%. Similarly, if the determined longitudinal location of the implanted neuromodulation lead 12 is the sacral region of the vertebral column (S1-S5), the selected percentage of the perception threshold from which to calculate the sub-threshold amplitude is 60%.

It should be appreciated that the above mentioned vertebral levels and percentages are exemplary only, and that different embodiments may use other and/or similar percentages. As a general rule, the percentage for the cervical region of the spinal cord typically ranges from 20%-60% of the perception threshold, the percentage for the thoracic region of the spinal cord typically ranges from 30%-70% of the perception threshold, the percentage for the lumbar region of the spinal cord typically ranges from 40%-80% of the perception threshold, and the percentage for the sacral region of the spinal cord typically ranges from 50%-90% of the perception threshold. As mentioned previously, the look-up table may use any percentages that fall within the above mentioned ranges for each vertebral level in selecting the percentage to be used in calculating the sub-threshold amplitude. It should be appreciated that certain embodiments may illustrate the calculated sub-threshold amplitude in the sub-threshold amplitude screen 200, while others may display the calculated sub-threshold amplitude in the manual programming screen 100.

Figure 10:
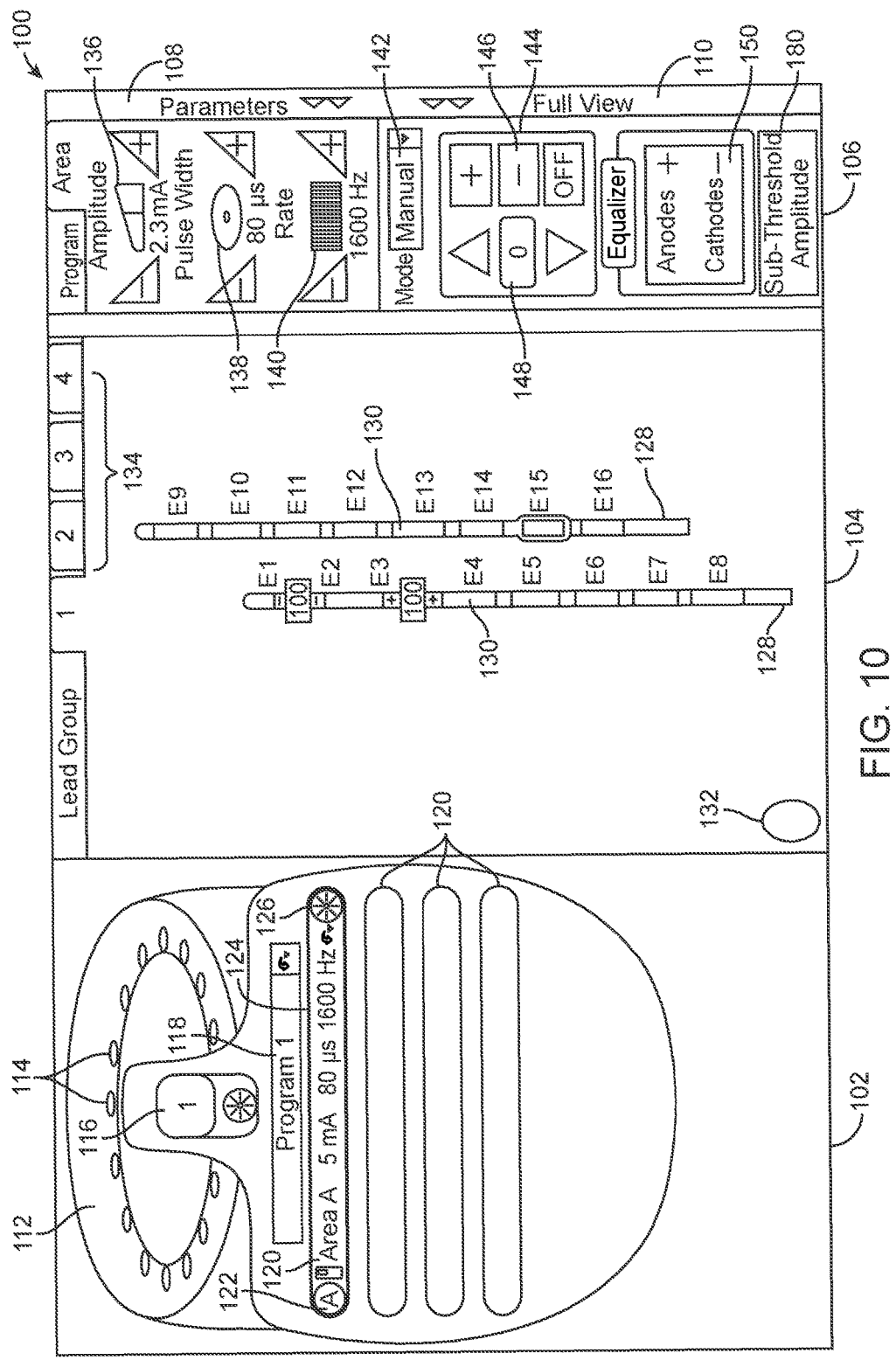
FIG. 10 is the plan view of the manual programming mode of FIG. 7 illustrating the automatically selected sub-threshold amplitude based on the table of FIG. 9.

In the illustrated embodiment, once the perception threshold has been determined, the user may actuate the "OK" button 250 to be automatically taken back to the manual programming mode screen 100. Assuming that the determined longitudinal location of the neuromodulation lead 12 is in the sacral region, the calculated sub-threshold amplitude is 2.3 mA (i.e., 60% of the perception threshold set at 3.8 mA), as shown in the parameter adjustment panel 102 of the manual programming screen, illustrated in FIG. 10. It should be appreciated that the generated sub-threshold amplitude may be modified based on user discretion using graphical controls 136.

In a preferred embodiment, the sub-threshold amplitude and/or a range of sub-threshold amplitudes may be additionally stored into the RC 16 such that the patient can maintain some control over the programming of the IPG 14 at home. For example, if the patient wants to modify the sub-threshold amplitude (or other modulation parameters), he may easily do so with the RC 16.

To this end, the acceptable ranges of sub-threshold amplitude for the determined longitudinal location of the implanted neuromodulation lead 12 may be automatically stored in the RC 16. For example, if the determined location of the neuromodulation lead 12 is the sacral region, even though the sub-threshold amplitude is currently set at 60% of the perception threshold in the illustrated embodiment as per the look-up table of FIG. 9, the patient may be able to modify the sub-threshold amplitude as long as it stays within the preferred range of 50%-90% of the perception threshold for the sacral region (i.e., 1.9 mA to 3.42 mA). Or, if the determined location of the neuromodulation lead 12 is the cervical region, even though the sub-threshold amplitude may be set at 1.14 mA (not shown) the patient may be able to modify the sub-threshold amplitude as long as it stays within the preferred range of 20%-60% of the perception threshold for the cervical region (i.e., 0.76 mA to 3.04 mA). The ranges of the thoracic and lumbar regions may be similarly stored to allow for modification of the sub-threshold amplitude based on patient discretion.

In an alternate embodiment, the user may define (not illustrated), a minimum amplitude level and a maximum amplitude level such that the patient, at his/her own discretion, is able to adjust the sub-threshold amplitude within a range. For example, assuming that the sub-threshold amplitude level is set at 60% of the perception threshold, the minimum amplitude level may be defined as 50% of the perception threshold, and the maximum amplitude may be defined as 70% of the perception threshold. Or, in another example, if the user wants therapy to remain at a tighter range, the minimum amplitude may be set at 55% of the perception threshold and the maximum amplitude may be set at 65% of the perception threshold.

Thus, by automatically selecting the appropriate percentage of the perception threshold from which to calculate the sub-threshold amplitude, the SCM system 10 accounts for the differences in neural tissue along the spinal cord, thereby making the process of finding an optimal sub-threshold modulation regimen for the patient easier and more efficient.

Although the illustrated embodiments have focused on using the manual programming mode, it should be appreciated that any of the other programming modes of the CP 18 may also be similarly used.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for use with a neuromodulation lead having at least one electrode configured for being implanted along a spinal cord of a patient, the system comprising:
    modulation output circuitry configured to deliver sub-threshold modulation energy to the at least one electrode; and
    control/processing circuitry configured to determine an amplitude value for subthreshold energy as a function of a longitudinal location of the neuromodulation lead relative to the spinal cord.

2. The neuromodulation system of claim 1, wherein the control/processing circuitry is configured to determine the longitudinal location of the implanted neuromodulation lead relative to the spinal cord.

3. The neuromodulation system of claim 1, further comprising a user interface configured to receive as user input the longitudinal location of the implanted neuromodulation lead relative to the spinal cord.

4. The neuromodulation system of claim 1, wherein the at least one electrode is more than one electrode, and the control/processing circuitry is configured to compute the amplitude value as a function of a fractionalized electrode configuration that determines a relative percentage of modulation energy assigned to each of the more than one electrode.

5. The neuromodulation system of claim 4, wherein the selected percentage is a first percentage when the longitudinal location is in a first region of the spinal cord, and the selected percentage is a second percentage when the longitudinal location is in a second region of the spinal cord, wherein the second percentage is higher than the first percentage, and the second region of the spinal cord is caudal to the first region of the spinal cord.

6. The neuromodulation system of claim 4, wherein the selected percentage is a first percentage when the longitudinal location is in a cervical region of the spinal cord, the selected percentage is a second percentage when the longitudinal location is in a thoracic region of the spinal cord, the selected percentage is a third percentage when the longitudinal location is in a lumbar region of the spinal cord, and the selected percentage is a fourth percentage when the longitudinal location is in a sacral region of the spinal cord, wherein the second percentage is greater than the first percentage, the third percentage is greater than the second percentage, and the fourth percentage is greater than the third percentage.

7. The neuromodulation system of claim 6, wherein the fourth percentage is in the range of 50%-90% of a perception threshold, the third percentage is in the range of 40%-80% of the perception threshold, the second percentage is in the range of 30% -70% of the perception threshold, and the first percentage is in the range of 20%-60% of the perception threshold.

8. The neuromodulation system of claim 1, further comprising memory storing a look-up table containing neuromodulation lead locations and a percentage associated with each of the neuromodulation lead locations, wherein the control/processing circuitry is configured to match the longitudinal location of the neuromodulation lead relative to the spinal cord with one of the neuromodulation lead locations stored in the look-up table and select the percentage associated with the matched neuromodulation lead location.

9. An external controller for use with a neuromodulation device coupled to at least one electrode, the external controller comprising:
a user interface configured to receive user input; and
control/processing circuitry configured to select a percentage of a perception threshold based on a longitudinal location of the neuromodulation lead relative to the spinal cord.

10. The external controller of claim 9, wherein the control/processing circuitry is configured to determine the longitudinal location of the implanted neuromodulation lead relative to the spinal cord.

11. The external controller of claim 9, wherein the user interface is further configured to receive as user input the longitudinal location of the implanted neuromodulation lead relative to the spinal cord.

12. The external controller of claim 9, wherein the at least one electrode is more than one electrode, and the control/processing circuitry is configured to compute an amplitude value as a function of a fractionalized electrode configuration that determines a relative percentage of modulation energy assigned to each electrode.

13. The external controller of claim 12, wherein the selected percentage is a first percentage when the longitudinal location is in a first region of the spinal cord, and the selected percentage is a second percentage when the longitudinal location is in a second region of the spinal cord, wherein the second percentage is higher than the first percentage, and the second region of the spinal cord is caudal to the first region of the spinal cord.

14. The external controller of claim 12, wherein the selected percentage is a first percentage when the longitudinal location is in a cervical region of the spinal cord, the selected percentage is a second percentage when the longitudinal location is in a thoracic region of the spinal cord, the selected percentage is a third percentage when the longitudinal location is in a lumbar region of the spinal cord, and the selected percentage is a fourth percentage when the longitudinal location is in a sacral region of the spinal cord, wherein the second percentage is greater than the first percentage, the third percentage is greater than the second percentage, and the fourth percentage is greater than the third percentage.

15. The external controller of claim 14, wherein the fourth percentage is in the range of 50%-90% of the perception threshold, the third percentage is in the range of 40%-80% of the perception threshold, the second percentage is in the range of 30% -70% of the perception threshold, and the first percentage is in the range of 20%-60% of the perception threshold.

16. The external controller of claim 9, further comprising memory storing a look-up table containing neuromodulation lead locations and a percentage associated with each of the neuromodulation lead locations, wherein the control/processing circuitry is configured to match the longitudinal location of the neuromodulation lead relative to the spinal cord with one of the neuromodulation lead locations stored in the look-up table and select the percentage associated with the matched neuromodulation lead location.

17. A method, comprising:
determining an amplitude value for subthreshold modulation energy as a function of a longitudinal location of the neuromodulation lead relative to the spinal cord; and
providing a subthreshold modulation therapy, including delivering the sub-threshold modulation energy at the determined amplitude.

18. The method of claim 17, further comprising:
determining the longitudinal location of the neuromodulation lead relative to the spinal cord.

19. The method of claim 17, further comprising:
receiving as user input the longitudinal location of the implanted neuromodulation lead relative to the spinal cord.

20. The method of claim 17, wherein delivering the sub-threshold modulation energy includes using electrodes to deliver the sub-threshold modulation energy, the method further comprising computing an amplitude value as a function of a fractionalized electrode configuration that determines a relative percentage of modulation energy assigned to each electrode.

* * * * *